US012600835B2

(12) United States Patent
Dugar et al.

(10) Patent No.: US 12,600,835 B2
(45) Date of Patent: Apr. 14, 2026

(54) SOLVENT APPLICATIONS OF ANHYDROMEVALONOLACTONE

(71) Applicant: Visolis, Inc., Berkeley, CA (US)

(72) Inventors: Deepak Dugar, Berkeley, CA (US); Mustafa J. Bootwala, Fremont, CA (US); Cecelia Rivera, Berkeley, CA (US); Chance Plaskett, Oakland, CA (US)

(73) Assignee: Visolis, Inc., Dallas, TX (US)

( * ) Notice: Subject to any disclaimer, the term of this patent is extended or adjusted under 35 U.S.C. 154(b) by 800 days.

(21) Appl. No.: 17/292,684

(22) PCT Filed: Nov. 8, 2019

(86) PCT No.: PCT/US2019/060387
§ 371 (c)(1),
(2) Date: May 10, 2021

(87) PCT Pub. No.: WO2020/097413
PCT Pub. Date: May 14, 2020

(65) Prior Publication Data
US 2022/0010091 A1     Jan. 13, 2022

Related U.S. Application Data

(60) Provisional application No. 62/757,905, filed on Nov. 9, 2018.

(51) Int. Cl.
| | |
|---|---|
| *C08J 11/08* | (2006.01) |
| *C07D 309/32* | (2006.01) |
| *C09D 9/00* | (2006.01) |

(52) U.S. Cl.
CPC ............ *C08J 11/08* (2013.01); *C07D 309/32* (2013.01); *C09D 9/005* (2013.01); *C08J 2321/02* (2013.01); *C08J 2327/06* (2013.01); *C08J 2327/16* (2013.01); *C08J 2333/12* (2013.01); *C08J 2333/20* (2013.01); *C08J 2363/00* (2013.01); *C08J 2367/04* (2013.01); *C08J 2369/00* (2013.01); *C08J 2377/02* (2013.01); *C08J 2379/02* (2013.01)

(58) Field of Classification Search
CPC ...................................................... C08J 11/08
See application file for complete search history.

(56) References Cited

U.S. PATENT DOCUMENTS

| | | | | | |
|---|---|---|---|---|---|
| 4,675,354 | A | * | 6/1987 | Sperling | ................. C09J 201/00 156/332 |
| 4,957,833 | A | * | 9/1990 | Daifuku | ................. H01M 10/05 429/213 |
| 8,557,447 | B2 | | 10/2013 | Lee | |
| 2002/0039688 | A1 | * | 4/2002 | Barker | .............. H01M 10/0569 429/223 |
| 2004/0081846 | A1 | * | 4/2004 | Shimizu | ............... C09D 181/02 428/524 |
| 2008/0085990 | A1 | * | 4/2008 | Richter | .................. C08G 65/46 528/126 |
| 2008/0131783 | A1 | * | 6/2008 | Choi | .................... H01M 4/622 252/182.1 |
| 2011/0300450 | A1 | * | 12/2011 | Balaji | .............. H01M 10/0565 429/303 |
| 2016/0068877 | A1 | * | 3/2016 | Zhang | .................. C07D 309/30 435/254.2 |
| 2016/0145227 | A1 | * | 5/2016 | Dugar | .................... C07C 45/66 585/324 |

FOREIGN PATENT DOCUMENTS

| | | |
|---|---|---|
| DE | 19918761 A1 | 10/2020 |
| JP | 4854110 B2 | 6/2002 |
| JP | 09208419 A | 6/2004 |
| WO | 2021041361 A1 | 3/2021 |
| WO | 2021041363 A1 | 3/2021 |

OTHER PUBLICATIONS

Benzene flyer, Wikipedia (Year: NA).*
Chemical Properties of Dehydromevalonic Lactone flyer, 2013 (Year: 2013).*
4-methyl-2,3-dihydropyran-6-one flyer, Molbase flyer (Year: NA) (Year: NA).*
Dehydromevalonolactone, Encyclopedia, LookChem, 2008 (Year: 2008).*
Search Report and Written Opinion dated Feb. 20, 2020 for related PCT Patent Application No. PCT/US2019/060387, 14 pages.

* cited by examiner

*Primary Examiner* — Irina Krylova
(74) *Attorney, Agent, or Firm* — Hovey Williams LLP; Kameron D. Kelly

(57) ABSTRACT

Described herein are solvents and co-solvents comprising anhydromevalonolactone (aMVL) and various industrial applications for such solvents. aMVL has a number of advantageous properties for use in solvent, including high boiling point, low melting point, low viscosity, non-flammability, water solubility, exceptionally low volatility, and excellent solvation capability. Exemplary industrial applications for solvents comprising aMVL include polymer manufacturing, polymer recycling, mold production, fiber production, membrane manufacturing, thermosetting paint manufacturing, coating manufacturing, coating removal, paint strippers, cleaning products, degreasing products, nitrile synthesis, alkylation, production of syngas, carbon-carbon cross-coupling reactions, metal organic framework synthesis, halogenation reactions, formation of pharmaceuticals, formation of fungicides and/or herbicides, seed treatment products, bioregulators, and electrolytes in batteries or capacitors.

9 Claims, 5 Drawing Sheets

SOLVENT APPLICATIONS OF ANHYDROMEVALONOLACTONE

RELATED APPLICATIONS

The present application claims the priority benefit of PCT Patent Application No. PCT/US2019/060387, filed Nov. 8, 2019, entitled SOLVENT APPLICATIONS OF ANHYDROMEVALONOLACTONE, which claims the priority of benefit of U.S. Provisional Application No. 62/757,905, filed Nov. 9, 2019, entitled SOLVENT APPLICATIONS OF ANHYDROMEVALONOLACTONE, of which are incorporated by reference in their entirety herein.

BACKGROUND OF THE INVENTION

Field of the Invention

The present invention is generally directed to solvents comprising anhydromevalonolactone and various industrial uses thereof.

Description of the Prior Art

Solvents are ubiquitous in chemical industries. They are used in varying concentrations and under different conditions across industries as diverse as paper and pulp processing to pharmaceuticals. Depending on the applications they are applied as cleaning, working or recycling fluids.

Two of the most widely used solvents today are NMP and DCM with a combined market size of 1.4 million tonnes per annum in 2014. The largest application for NMP and DCM are in polymer dissolution and paint stripping, respectively. Use of both the solvents, however, poses significant health hazards including: acute neurotoxicity, organ damage, carcinogenicity, teratogenicity and muscular deformation [EPA-740-R1-7005, EPA-740-R1-7004].

SUMMARY OF THE INVENTION

The bio-derived molecule, anhydromevalonolactone (4-methyl-5,6-dihydro-2H-pyran-2-one or aMVL), is described herein for its performance as a solvent for a variety of applications. This polar molecule has many attractive properties including high boiling point (200-250° C.), low melting point (−40-20° C.), low viscosity (3-5 mPas), non-flammability, water solubility (~600-900 g/L), exceptionally low volatility (vapor pressure: 30-40 Pa at 67° C.), and excellent solvation capability (according to Hansen solubility parameters). aMVL can be made inexpensively by dehydration of mevalonolactone (MVL), a bio-intermediate that can be produced in high yields via fermentation using a variety of biomass feedstock, making aMVL a green and readily accessible bio-based molecule [US Patent Application Publication No. 2016/0145227, incorporated herein in its entirety]. Based on Hansen solubility parameters, (a system that quantifies the likelihood of dissolution of one material in another), aMVL operates similarly to DCM and NMP in terms of solvation capabilities.

An objective of the present invention is to demonstrate aMVL's performance and applicability for a variety of solvent applications and its use in place of the more hazardous polar aprotic solvents like NMP, DCM and/or ethers. The aforementioned applications include but are not limited to the use of aMVL as a solvent, reaction medium, dehydrating agent, diluent, extracting medium, cleaning agent, degreaser, absorbent and/or dispersant. Furthermore, the present invention provides for the use of aMVL for paint removal, battery electrolyte and as a metalworking fluid.

In one embodiment, there is provided a solvent for one or more industrial applications. The solvent comprises anhydromevalonolactone.

In another embodiment, there is provided a process for producing a solvent for an industrial application. The process comprises the steps of: (a) forming a solvent comprising anhydromevalonolactone; and (b) providing the solvent to the industrial application.

In another embodiment, there is provided a process for producing or recycling a polymer. The process comprises the steps of: (a) providing a solvent comprising anhydromevalonolactone; and (b) producing a polymer or recycling the polymer in the presence of the solvent.

In another embodiment, there is provided an electrolytic capacitor. The electrolyte capacitor comprises an anode, a cathode, and an electrolyte. The electrolyte comprises a solvent. The solvent comprises anhydromevalonolactone.

In another embodiment, there is provided a process for removing oil, grease, a coating, paint, or stain from a surface. The process comprises the steps of (a) providing a solvent comprising anhydromevalonolactone; and (b) applying the solvent to the surface.

In another embodiment, there is provided the use of anhydromevalonolactone as a solvent in one or more industrial applications.

In another embodiment, there is provided a process for recycling a polymer. The process comprises at least the following steps:

- (a) dissolving at least one scrap polymer in a solvent selected from the group consisting of anhydromevalonolactone, methyl ethyl ketone, benzyl acetate, ethyl benzoate, cyclohexanone, cyclopentyl methyl ether, dichloromethane, and co-solvents mixtures thereof, thereby forming a polymer mixture;
- (b) contacting the reaction mixture with an absorbent or adsorbent to form a purified polymer mixture;
- (c) contacting the purified polymer mixture with at least one anti-solvent to thereby recover a dissolved polymer and a residue stream comprising the solvent and the anti-solvent;
- (d) separating the residue stream into a recovered solvent stream and recovered anti-solvent stream;
- (e) filtering the dissolved polymer to form a first filtered polymer;
- (f) washing the first filtered polymer to form a washed polymer;
- (g) filtering the washed polymer to form a second filtered polymer; and
- (h) drying the second filtered polymer to form a final polymer product.

DETAILED DESCRIPTION

Figure 1:
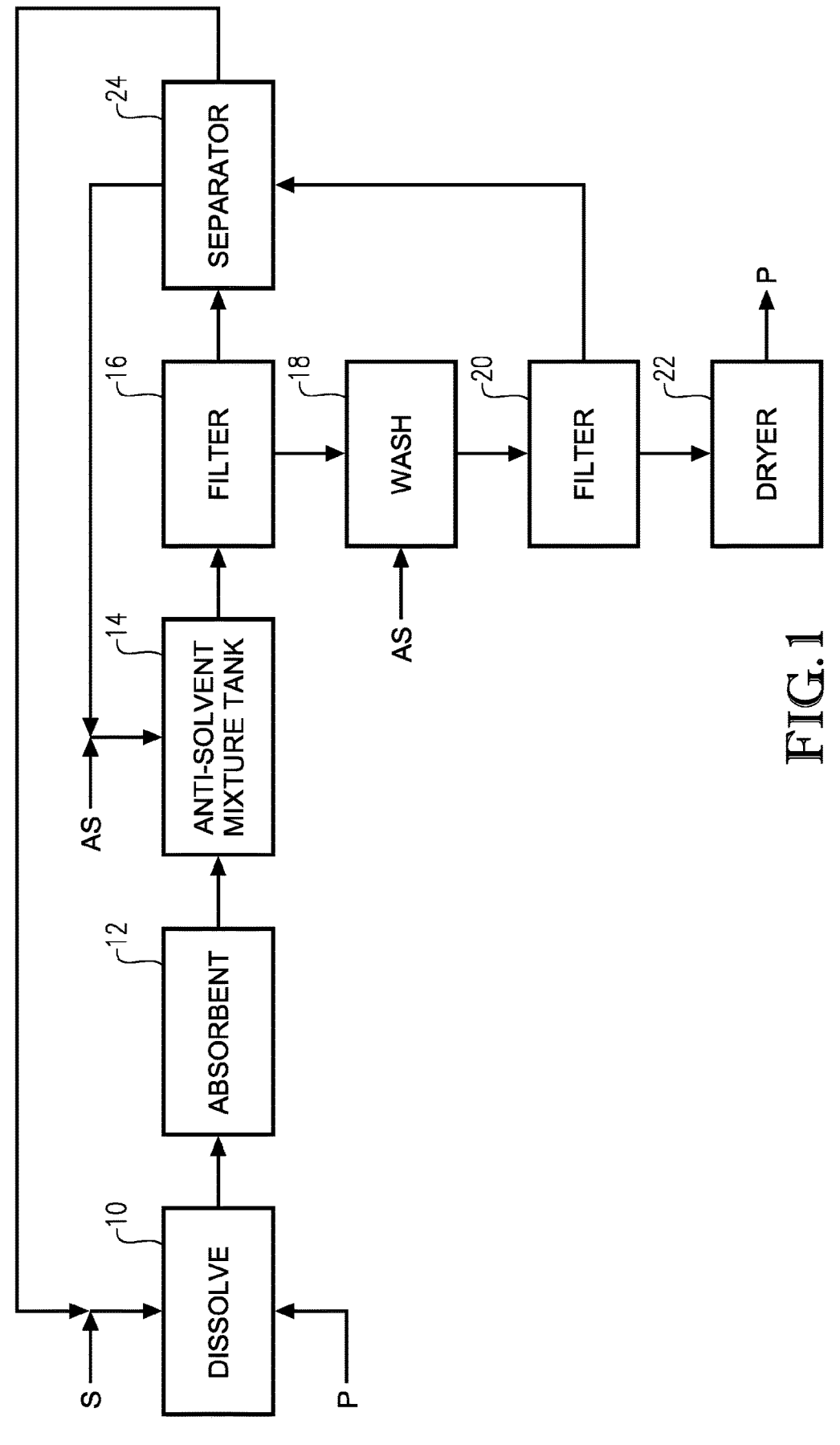
FIG. 1 is a schematic of a process to recover and recycle scrap polymer using aMVL and/or other co-solvents in accordance with one embodiment of the present invention.

Embodiments of the present invention are generally directed to solvents comprising anhydromevalonolactone (aMVL) and their use for one or more industrial applications. The solvent may be substantially pure aMVL or a co-solvent comprising a mixture of aMVL and one or more other components. In certain embodiments, the solvent comprises aMVL and or more co-solvents selected from the group consisting of methyl ethyl ketone, benzyl acetate, ethyl benzoate, cyclohexanone, cyclopentyl methyl ether, and dichloromethane. In certain other embodiments, the solvent consists of (or consists essentially of) aMVL. In certain embodiments, the solvent comprises about 10 to about 100 weight percent, preferably about 50 to about 99 weight percent of aMVL. In certain embodiments, the solvent comprises at least about 1, 5, 10, 15, 20, 25, 30, 35, 40, 45, 50, 55, 60, 65, 70, 75, 80, 85, 90, 95, or 99 weight percent of aMVL. The solvent generally has a boiling point of about 200 to about 250° C., preferably about 225 to about 240° C. The solvent generally has a melting point of about −40 to about 20° C., preferably about −30 to about −10° C. The solvent generally has a viscosity of about 3 to about 5 mPa·s at standard ambient temperature and pressure. The solvent generally has a water solubility of about 600 to about 900 g/L, preferably about 750 to about 850 g/L at standard ambient temperature and pressure. The solvent generally has a vapor pressure of about 30 to about 40 Pa at 67° C.

The solvent comprising aMVL may be used in a variety of different industrial applications, a number of which are described in greater detail herein. Exemplary industrial applications include a polymer manufacturing process, a polymer recycling process, a mold production process, a fiber production process, a membrane manufacturing process, a thermosetting paint manufacturing process, a coating manufacturing process, coating removal, paint strippers, cleaning products, degreasing products, nitrile synthesis, alkylation, production of syngas, carbon-carbon cross-coupling reactions, metal organic framework synthesis, halogenation reactions, formation of pharmaceuticals, formation of fungicides and/or herbicides, seed treatment products, bio-regulators, electrolytes in batteries or capacitors, or combinations thereof. Therefore, certain embodiments of the present invention are directed to a process for producing a solvent for an industrial application. The process comprises the steps of: (a) forming the solvent comprising aMVL; and (b) providing the solvent to the industrial application. Specific industrial applications using the aMVL solvent are described in the description and examples below.

Polymer Manufacturing Applications

In one or more embodiments of the present invention, the solvent is used in a process for producing, modifying, and/or recycling a polymer (including co-polymer). In certain embodiments, the solvent is used in a process for producing a polymer comprising the steps of: (a) providing a solvent comprising aMVL; and (b) producing a polymer in the presence of the solvent. The polymer can be produced using a variety of techniques due to the properties of the solvent comprising aMVL, with or without other co-solvents.

In one embodiment, the solvent comprising aMVL can be used to dissolve one or more polymers. In certain embodiments, the one or more polymers comprises (consists of, or consists essentially of) a polymer selected from the group consisting of polysulfones, polyesters, polycarboxylic acids, polyanhydrides, polyacrylates, polyacrylamide, polyacrylonitrile, polyvinylchloride, polyvinylesters, polyamides, polyimides, poly amide-imides, polyvinylacetals, polyoxyalkylenes, polystyrene, polycarbonate, polyurethanes, polyureas, and co-polymers thereof. Since aMVL has high solubility with the corresponding monomers, conventional organic solvents and water, unique and optimal solvent blends for a given application can be used. Thus, in certain embodiments, the process of producing the polymer comprises the step of dissolving the polymer in the solvent comprising aMVL.

In one embodiment, the solvent comprising aMVL is used to prepare moldings. The solvents described herein are particularly useful for such applications because aMVL is non-corrosive, non-flammable and allows for highly concentrated solutions of moldable compounds to be produced from a range of polymers. Thus, in certain embodiments, the process of producing the polymer comprises the step of forming a concentrated solution comprising a polymer in the solvent. In certain such embodiments, the polymer is selected from the group consisting of polyacrylonitrile, polyvinylchloride, polystyrene, and combinations thereof. By virtue of its swelling and solubilizing action, the solvent comprising aMVL can also be used for cold-wetting of plastics.

In one embodiment, the solvent comprising aMVL readily dissolves polymers such as polyacrylonitrile, aromatic polyamides, polyureas, polyvinyl esters and alcohols and/or copolymers thereof. Thus, in certain preferred embodiments, the process of producing the polymer comprises the step of dissolving one or more of the above polymers and/or copolymers in the solvent comprising aMVL. Most of these do not dissolve or are sparingly soluble in other solvents. Thus, the use of aMVL with or without additives is an excellent medium to solvate these polymers for spinning and extruding into fibers.

In another embodiment, polymers such as polysulfones and polycarbonates are widely used to manufacture membranes in separation processes like ultrafiltration, osmosis and gas purification. aMVL can be used as a solvent for the production of such membranes due to its high solvation capabilities of the polymer material. Thus, in certain preferred embodiments, the process of producing the polymer comprises the step of dissolving one or both of polysulfones and polycarbonates in the solvent comprising aMVL.

In another embodiment, since aMVL is a non-corrosive high boiling compound with excellent solvation abilities and chemical resistance it is a solvent favorable for baked coatings that are cured at temperatures between about 80° C. to about 150° C. aMVL can improve rheological properties, which leads to paints and finishes with superior flow-out and higher covering power. Hence, the coatings are more homogeneous, non-porous, display greater resistance to chemicals and possess higher mechanical strength. aMVL is an excellent solvent for most coating raw materials such as but not limited to acrylate, polyurethanes, polyvinylchloride systems, polyamide-imide based wire enamels, water-based coatings and printing inks optionally containing a UV curable resin. Thus, in certain preferred embodiments, the process of producing the polymer comprises the step of dissolving one or more of the above-listed components in the solvent comprising aMVL.

In another embodiment, aMVL can be used as the medium during production of thermosetting paints for electrical insulation. Polyisocyanates containing amide groups can be formed in the condensation reaction between aMVL solutions of polybasic carboxylic anhydrides and monomeric polyvalent isocyanates. The resulting polyisocyanate finishes yield coatings with outstanding mechanical and dielectric properties particularly on copper conductors. aMVL in this application serves two purposes: first as a reaction medium in the manufacturing process; and second as a viscosity modifier since it remains in the final coating. Thus, in certain preferred embodiments, the process of producing the polymer comprises the step of reacting aMVL with a precursor (e.g., polybasic carboxylic anhydrides and monomeric polyvalent isocyanates) to form a reaction product (e.g., polyisocyanate) in the solvent comprising aMVL.

Since aMVL is non-corrosive, high boiling, and relatively inert under most conditions, in one embodiment it can serve as an excellent solvent for polymerization reactions. Most free radical polymerization initiators (AIBN, BPO, TMA and DTBP) show no effect on aMVL. In addition, aMVL is applicable as a solvent for ring opening polymerization reactions since aMVL does not ring open unless under extremely basic conditions, or high temperatures and H2 pressures. In particular, aMVL can be used for the production of polycarboxylic acids, polyesters, polyvinyl esters, polycarbonate, polysulfones, polyamides and polyamide-imides. Thus, in certain preferred embodiments, the process of producing the polymer comprises the step of mixing a polymerization initiator and/or one or more monomers in the solvent comprising aMVL. Exemplary monomers include MMA and styrene.

In certain embodiments, all or a portion of the producing step occurs at a temperature of about 20 to about 200° C., preferably about 40 to about 180° C., and more preferably about 60 to about 150° C. In certain embodiments, the all or a portion of the producing step occurs at a pressure of about 0.01 to about 20 MPa, preferably about 0.05 to about 15 MPa, and more preferably about 0.1 to about 10 MPa. In certain embodiments, and particularly when polymer is dissolved in the solvent comprising aMVL, the polymer is present in the solution as a concentration of about 1 to about 90 weight percent, preferably about 2 to about 50 weight percent, and more preferably about 5 to about 25 weight percent. In certain embodiments, the contact time to achieve dissolution of the polymer in solvent is about 0.5 to about 48 hours, preferably about 1 to about 24 hours, and more preferably about 2 to about 12 hours. In certain embodiments, and particularly in embodiments for polymer synthesis, the monomer concentration in the reaction mixture comprising the solvent is about 0.1 to about 90 weight percent, preferably about 0.2 to about 49 weight percent, and more preferably about 5 to about 25 weight percent. In certain such embodiments, the reaction mixture comprises the initiator at a concentration of about 0.1 to about 10 weight percent, preferably about 1 to about 5 weight percent.

Polymer Recycling Applications

In one or more embodiments of the present invention, a solvent, and in certain embodiments the solvent comprising aMVL, can be used to recover and recycle scrap polymer. The process generally comprises the steps of: (a) providing a solvent; and (b) recycling the polymer in the presence of the solvent. In certain embodiments, the solvent is selected from the group consisting of aMVL, methyl ethyl ketone, benzyl acetate, ethyl benzoate, cyclohexanone, cyclopentyl methyl ether, dichloromethane, and co-solvents mixtures thereof. In certain embodiments, the solvent comprises substantially pure aMVL. In certain embodiments, the solvent comprises aMVL and a co-solvent selected from the group consisting of methyl ethyl ketone, benzyl acetate, ethyl benzoate, cyclohexanone, cyclopentyl methyl ether, and dichloromethane. In certain such embodiments, the solvent comprises at least about 10, 50, 80, 90, or 99 weight percent of aMVL, with the total weight of the solvent (including co-solvent) taken as 100 percent by weight. However, in other such embodiments, the solvent comprises less than about 1, 0.5, or 0.1 weight percent of aMVL, with the total weight of the solvent (including co-solvent) taken as 100 percent by weight. The polymer recycling process may incorporate one or more of the techniques described above and may utilize the same or different temperatures, pressures, contact times, and/or concentrations described for polymer production.

An exemplary polymer recycling process is shown in FIG. 1. Scrap Polymer, P is dissolved in the solvent solution, S in unit operation 10 at conditions best optimized for dissolution to form a polymer mixture. In certain preferred embodiments, the scrap polymer is a polymer or copolymer selected from the group consisting of polymers and/or copolymers are polysulfones, polyesters, polycarboxylic acids, polyanhydrides, polyacrylates, polyacrylamide, polyacrylonitrile, polyvinylchloride, polyvinylesters, polyamides, polyimides, poly amide-imides, polyvinylacetals, polyoxyalkylenes, polystyrene, polycarbonate, polyurethanes, polyureas, and co-polymers thereof.

The solution comprising the polymer mixture is then passed through a bed 12 to contact adsorbent or absorbent and remove color, dyes, fillers and other impurities, thereby forming a purified polymer mixture. In certain embodiments, the adsorbent or absorbent comprises one or more of silica, activate charcoal, ion exchange resins, diatomaceous earth, montmorillonite and zeolites. The solution comprising purified polymer mixture is then contacted with optimal anti-solvent, AS in tank 14 to recover dissolved polymer and produce a residue stream comprising the solvent and anti-solvent. In certain embodiments, the anti-solvent is selected from the group consisting of water, inorganic acid solutions, inorganic alkali solutions, alcohols, aromatics, esters, ethers, aldehydes, amines, ketones, organohalides, amides, lactones, lactams, C5-C10 olefins, C5-C10 hydrocarbons, and C5-C15 terpene or admixtures thereof. In preferred embodiments, the anti-solvent comprises water and/or ethanol. In certain embodiments, the ratio of solvent to anti-solvent is about 10:1 to about 1:10, preferably about 5:1 to about 1:5, and more preferably about 4:1 to about 1:4.

The precipitated polymer is then filtered 16, washed 18 and filtered 20 again. This filtered polymer is then dried in unit 22 to recover the final polymer. The residue stream comprising the solvent and anti-solvent (S/AS) mixture is then treated to a separation step in unit 24 which may include but is not limited to flash distillation, continuous distillation, extractive distillation, azeotropic distillation, evaporation, absorption, membrane separation or liquid-liquid extraction. This produces a recovered solvent stream and a recovered anti-solvent stream from separator unit 24. The recovered solvent stream can be recycled and combined with the solvent during the dissolving in unit operation 10. The anti-solvent stream can be recycled and combined with the anti-solvent during the contacting in anti-solvent mixture tank 14.

Other Solvent Applications

In one or more embodiments, the solvent comprising aMVL can be used for removing oil, grease, a coating, paint, or stain from a surface. The process comprises the steps of: (a) providing a solvent comprising anhydromevalonolactone; and (b) applying the solvent to the surface. Specific embodiments of this and other uses (and related compositions and processes) are described below.

Due to its high solvating power for oil and grease, in one embodiment aMVL can successfully be employed as an ingredient in cleaners and degreasers. Its miscibility with water and most conventional organic solvents allows for the manufacture of highly effective products, which can be tailored for use in different applications. The solvent comprising aMVL can be used alone or in blends and/or with additives for the removal of oil, carbon deposits and other tarry polymeric residues from metal, glass, ceramic, wooden and other surfaces. Blends of aMVL may be used for the cleaning of articles or surfaces soiled by oil, fat, soot, glue and the like by immersion in a bath. In another embodiment, aMVL can be used for the degreasing of metals before surface treatment. In a specific embodiment, aMVL based cleaning products can be used on outdoor/indoor walls for graffiti removal and for ultrasonic cleaning of items such as optical lenses or dental prostheses.

In one embodiment, aMVL can be used as a low VOC recyclable paint stripper. A paint stripper in this embodiment is defined as any solvent or mixture of solvents that can successfully dissolve industrial or commercial paints within a reasonably acceptable time frame. The high boiling point and high solubility of the solvent in water allows for efficient recycling, decreasing cost and environmental impact. It has performance similar to DCM while having a higher boiling point and a favorable toxicological profile. It can be mixed with other additives like esters, alcohols, ethers and water to modify paint activity to suit particular applications. Moreover, aMVL can be mixed with other solvents for the production of foaming-type coating remover, which is useful for removing various paints, varnishes, lacquers and other coatings or finishes, particularly from relatively large surfaces. These paint removers will be easy to use, low volatility, eco-friendly with reduced fire hazards. Particularly, aMVL can be used at concentrations of about 0.1 to about 99 weight percent with other additives for its use as a paint stripper.

Since aMVL is a chemically stable and powerful polar solvent, in one embodiment it can be used as a reaction medium for chemical reactions where an inert medium is desirable. Thus, in certain embodiments, the present invention is directed to the process of performing a chemical reaction in the presence of the solvent, diluent, or dispersant comprising aMVL. Some of these applications include but are not limited to: alkylation on acetylides, synthesis of nitriles and reaction medium for production of syngas. aMVL can also be used as dipolar aprotic solvent in carbon-carbon cross coupling reactions [Sonogashira, Suzuki-Miyaura, Heck] halogenation reactions and Metal Organic Framework (MOF) synthesis. Commonly used solvents for these reactions are NMP and N,N-dimethylformamide (DMF).

In another embodiment, aMVL can be used as a solvent or co-solvent for the formation of compounds used in but not limited to pharmaceuticals, insecticides, fungicides, herbicides, seed treatment products and bioregulators where a highly polar solvent is required.

In one embodiment, blends of aMVL with common solvents may be utilized for the cleaning and degreasing of single-crystal silicon wafers for ICs. In another embodiment, aMVL can be used as a solvent to remove residues of fluxing agents post soldering to prevent corrosion of the circuit boards. This may be accomplished with aMVL based solvent blends. In another embodiment, aMVL can be used for the selective removal of polymer coatings from certain areas on printed circuit boards.

In one or more embodiments, the aMVL is used in a process for modifying a polymer, which includes the production of moldings, inks, pigments, resins, dyes, fibers, wires, films, coatings, microparticles, nanoparticles, and membranes. In preferred embodiments, the solvent is used in the production of batteries and wires, specifically battery separators and wire enamels. The solvent comprising aMVL is particularly useful as an electrolyte solution in the presence of insoluble organic and inorganic solids. In certain embodiments, the solid is graphene and/or graphite. The solvent comprising aMVL is also particularly useful in the production of membranes of different porosities.

Figure 5C:
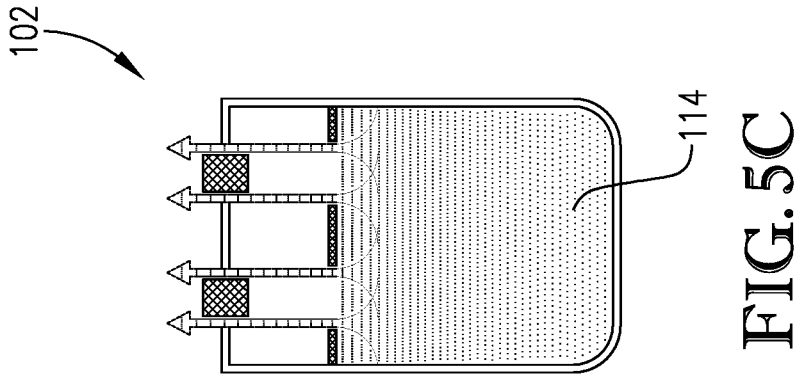
FIG. 5C is a schematic of the interior of the casing portion of the electrolytic capacitor of FIG. 5A.
Figure 5B:
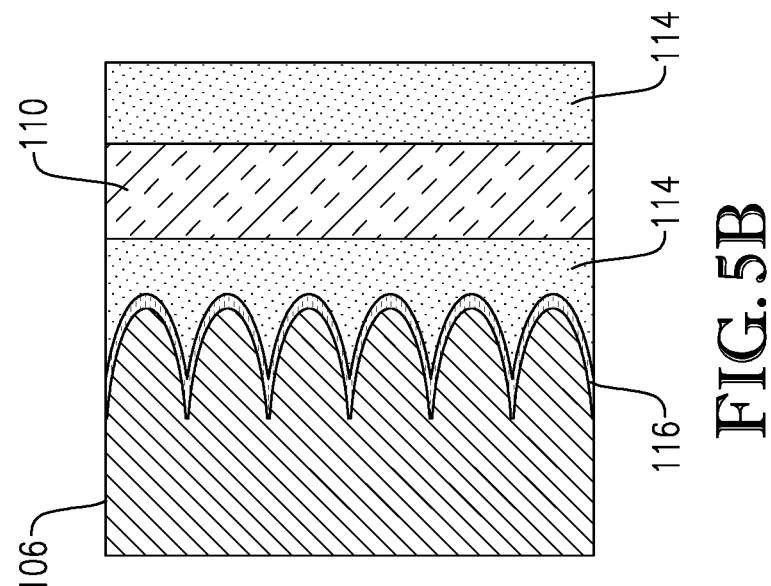
FIG. 5B is a close-up view of the electrode-electrolyte interface of the electrolytic capacitor of FIG. 5A.
Figure 5A:
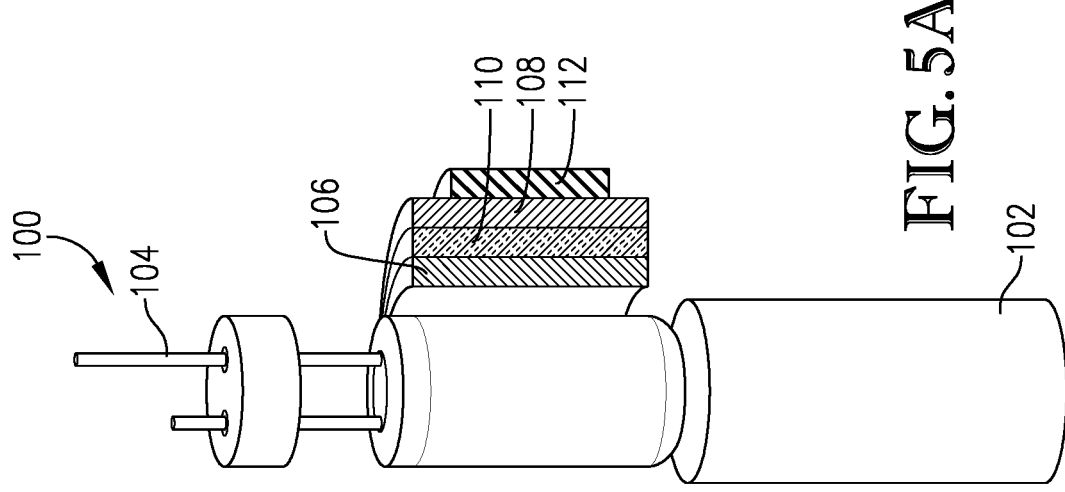
FIG. 5A is a perspective view of an electrolytic capacitor in accordance with one embodiment of the present invention.

In a preferred embodiment, aMVL is an advantageous electrolyte in battery or capacitors due to its high dielectric constant, low melting point and high boiling point. It can be used as an electrolyte in lithium ion or lithium air batteries or as an electrolyte in aluminum electrolytic capacitors for applications in electronics or automobiles. An exemplary electrolytic capacitor 100 is shown in FIGS. 5A, 5B, and 5C. Capacitor 100 comprises leads 104 and case 102 that houses the electrolyte solution comprising a solvent composition in accordance with embodiments of the present invention. Case 102 prevents leaking of the solvent electrolyte solution 114 and allows for evaporation of the solvent 114 into the interface of the separator membrane 110 and electrodes 106, 108. Anode 106 and cathode 108 may comprise, for example, an aluminum foil. Anode 106 further comprises an oxide film 116 formed on the rough surface facing separator membrane 110. An element stopped tape 112 may also be included adjacent cathode 108.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than or equal to about 10" (with no upper bounds) and a claim reciting "less than or equal to about 100" (with no lower bounds).

EXAMPLES

The following working and prophetic examples set forth experiments using solvents in accordance with embodiments of the present invention. It is to be understood, however, that these examples are provided by way of illustration and nothing therein should be taken as a limitation upon the overall scope of the invention.

Example 1

Polymer Solubility in aMVL

In Q-Tube glass pressure vessels, 2.17±0.2 g (2 mL) of aMVL and ~10 wt % of test polymers were loaded. The vessels were assembled with stir bars and placed on a hot plate. The aMVL and polymer containing solutions were stirred at 500 RPM, at 80° C. and atmospheric conditions for 24 h. After 24 h, the solutions were cooled to room temperature and filtered using a filter paper in a Buchner funnel. Residual polymer solids were rinsed using water, filtered and dried under $N_2$ gas. The final dried solid was weighed to determine the change in weight after contact with aMVL. Table 1 shows the results of this experiment.

TABLE 1

Polymer Solubility Data at 80° C. The table shows initial mass of the polymer taken, mass after mixing and drying and the change in polymer mass. Appearance of the solution and/or polymer solid is also noted for completion.

| Polymer | Initial Mass Polymer (g) | Final Mass Polymer (g) | ΔPolymer mass (g) | Solu-bility | Appearance |
|---|---|---|---|---|---|
| PAN | 0.1541 | — | −0.1541 | Yes | Clear |
| PVC | 0.2155 | — | −0.2155 | Yes | Viscous, Clear |
| PVDF | 0.2054 | 0.2064 | +0.0010 | No | Swelled Solid |
| PC | 0.1085 | 0.0064 | −0.1021 | Yes | Viscous |
| Epoxy | 0.0974 | 0.2121 | +0.1147 | No | Swelled Solid |
| Viton | 0.1093 | 0.1917 | +0.0824 | No | Swelled Solid |
| PEI | 0.7669 | — | −0.7669 | Yes | Clear liquid |
| PLA | 0.2136 | — | −0.2136 | Yes | Gel |
| Polystyrene | 0.201 | — | −0.2010 | Yes | Clear liquid |
| Nylon-12 | 0.2256 | 0.2264 | +0.008 | No | Solid |
| PMMA | 0.2218 | — | −0.2218 | Yes | Viscous, Clear |
| Latex | 0.1918 | 0.2065 | +0.0147 | No | Swelled Solid |

Example 2

Effect of Temperature on Polymer Solubility

The procedure described in Example 1 was performed at two temperatures, 80° C. and 150° C. The higher dissolution temperature allowed for the dissolution of certain polymers such as Nylon-12. The comparison of polymer solubility in aMVL between these two temperatures is shown in Table 2.

TABLE 2

Effect of temperature on polymer solubility.

| Polymer | Solubility at 80° C. | Appearance | Solubility at 150° C. | Appearance |
|---|---|---|---|---|
| Polystyrene | Yes | Clear liquid | Yes | Clear liquid |
| Nylon-12 | No | Solid | Yes | Clear yellow liquid |
| PMMA | Yes | Viscous, Clear | Yes | Clear liquid |
| Latex | No | Swelled solid | No | Swelled solid |

Example 3

Polymer Solubility in aMVL and Other Co-Solvents

50:50 mixtures and pure solutions of aMVL and other co-solvents were taken in a 20 mL scintillation glass vial with a working volume of 15 ml. 5% by mass scrap polycarbonate was added to the solutions. For low boiling co-solvents, the mixtures were heated to 38° C., while for higher boiling (>150° C.) co-solvents, the solutions were heated to 80° C., 100° C. or 120° C. This mixture was left stirring for 12 hours. After 12 hours the mixture was visually analyzed for solubility. Data on the mixtures is given in Table 3.

TABLE 3

Polycarbonate processing results for Examples 3, 4, 5 and 7.

| Solvent | Solvation temperature (° C.) | Result (Y/N) | Decolorization (Y/N) | Tg (° C.) | Average Mw (kDa) |
|---|---|---|---|---|---|
| aMVL | 80 | Y | Y | 143.95 | 37722 |
| DCM | 38 | Y | Y | — | — |
| Methyl Ethyl Ketone | 78 | N | — | — | — |
| Benzyl Acetate | 120 | Y | Y | 148.57 | 64492 |
| Ethyl Benzoate | 120 | Y | N | — | — |
| Cyclohexanone | 120 | Y | Y | 147.50 | 38366 |
| Cyclopentyl methyl ether | 100 | N | — | — | — |
| aMVL + Methyl Ethyl Ketone | 78 | N | — | — | — |
| aMVL + Benzyl Acetate | 120 | Y | Y | 147.94 | 45024 |
| aMVL + Ethyl Benzoate | 120 | Y | Y | 147.97 | 43882 |
| aMVL + Cyclohexanone | 120 | Y | Y | 140.06 | 36667 |
| aMVL + Cyclopentyl methyl ether | 100 | Y | N | — | — |
| Polycarbonate control | — | — | — | 142.73 | 42505 |

Example 4

Removing Color and Other Impurities from Polymer Solutions

Solutions of dissolved polymer from Example 3 were contacted with DARCO 20-40 mesh granular activated charcoal. Low viscosity solutions were gravity fed through 2 g of charcoal packed in a glass pipette. High viscosity solutions were contacted with 2 g of charcoal and gently shook for 1 min. After contact, the high viscosity solutions were filtered via a frit filter. Colorless polymer solutions were obtained after the adsorption treatment. Data on visual inspection is given in Table 3 above.

Example 5

Polymer Recovery with Anti-Solvent

Polymers that were found to be soluble in any of the mixtures from examples 1-4, forming liquid solutions or gels, and/or treated with activated charcoal were investigated for recovery using water, ethanol, or methanol as the anti-solvent at a ratio of 10:1 anti-solvent to dissolved solution. Dissolved polymer solution from the Examples 1, 2, 3 and 4 was added drop wise to a stirred beaker containing 10 times anti-solvent to solvent solution mass taken (providing the ratio noted above). The mixture was stirred for 30 min before gravity filtering out the polymer precipitate. The polymer was washed with the anti-solvent after the initial filtering was complete. Polymers analyzed and results are shown in Table 4.

TABLE 4

List of polymers tested for recovery.

| | Polymer | | | | | | | |
|---|---|---|---|---|---|---|---|---|
| | PC | PVC | PES | PLA | PAN | PMMA | PEI | Nylon 12 |
| Anti-solvents tested | EtOH/ H₂O/ MeOH | EtOH | H₂O | H₂O | H₂O | H₂O | H₂O | H₂O |

Example 6

Polymer Recovery by Evaporating Solvent

DCM-polycarbonate solution from example 3 was taken in a 100 ml round bottom flask in a rotary evaporator. The evaporator was set to a vacuum pressure of 12 mmHg and the water bath was kept at 40° C. The evaporator was stirred at 60 rpm. About half of the DCM was evaporated off. After this evaporation, about 15 ml of deionized water was added to the round bottom flask. Most of this solution was then evaporated at the same conditions. After this evaporation, the residual polymer was washed with 10 ml of deionized water, which was also removed via rotary evaporation. The residual polymer was dried in an oven overnight at 50° C.

Example 7

Analysis of Recovered Polymer after Color Removal

Figure 2:
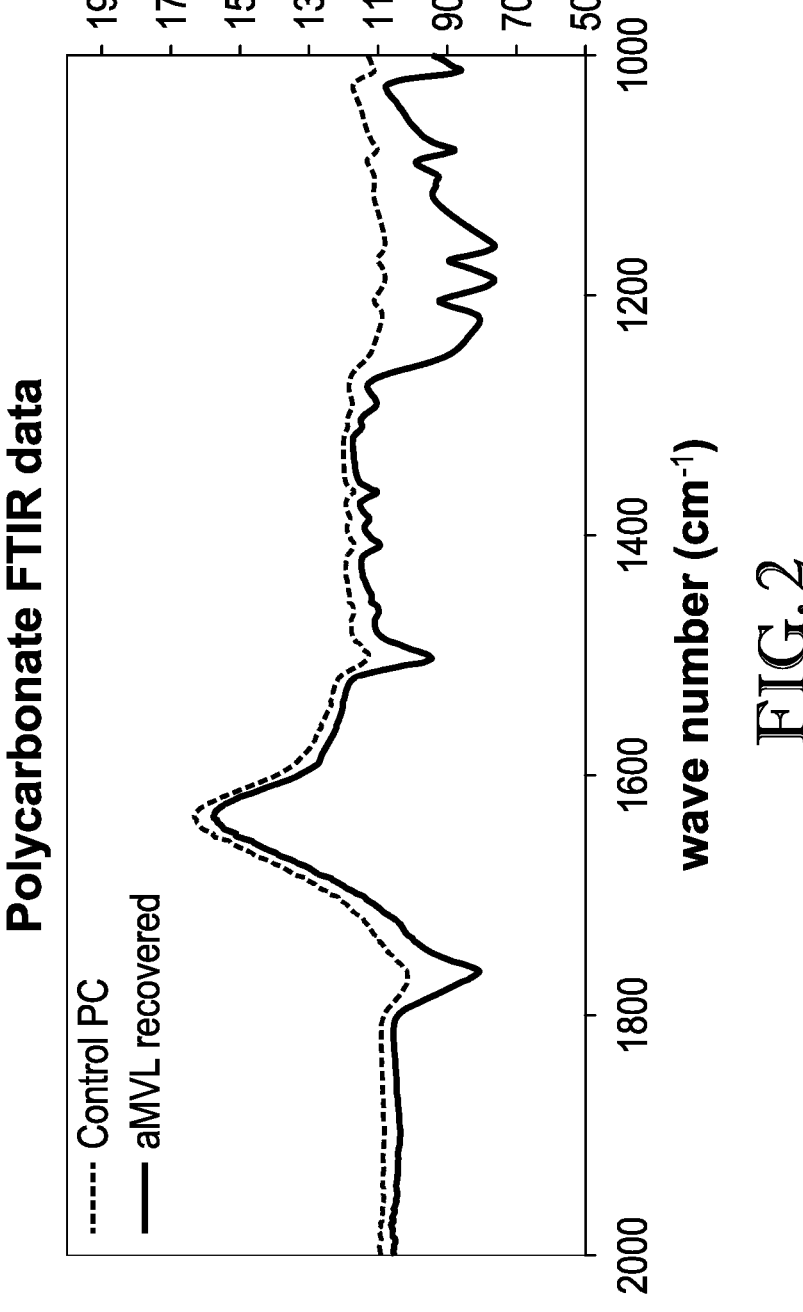
FIG. 2 is a graph showing FTIR data for recovered polycarbonate with aMVL and comparison to the control in accordance with one embodiment of the present invention.

Polycarbonate samples from example 4, precipitated in example 5 were analyzed by Differential Scanning Calorimeter (DSC), Fourier Transform Infrared spectroscopy (FTIR) and Gel Permeation Chromatography (GPC). These samples were compared with the starting scrap polycarbonate material. Data from GPC and DSC measurements is summarized in Table 3 above. FTIR data for recovered polycarbonate with aMVL and comparison to the control is given in FIG. 2.

Example 8

Effect of Polymerization Initiators on aMVL

~0.2 g of aMVL was mixed with ~0.2 g of styrene, methyl methacrylate (MMA) or prepared neat with ~10 mg of one or a mixture of the following polymerization initiators: Azobisisobutyronitrile (AIBN), Benzoyl peroxide (BPO), Trimethylaluminum (TMA) or Di-tert-butyl-peroxide (DTBP) or a 4:1 mixture of BPO:TMA. This mixture was solvated by 1 ml of solvent (deuterated chloroform, CDCl3, or deuterated benzene, C6D6) and sealed in an NMR tube inside a glovebox and heated to 75° C. At different time intervals the reaction mixture was analyzed by proton (1H) NMR to identify polymerization activity.

For neat solutions of aMVL with polymerization initiators, aMVL did not undergo any reaction through the course of the experiment, indicating that none of the polymerization initiators interacted with aMVL (Table 5, Entry 1-5). Polymerization of styrene (Table 5, Entry 6-9) and MMA (Table 5, Entry 10-12) using aMVL as a solvent was comparable to their polymerization using chloroform and benzene as solvents. Results are summarized in Table 5.

TABLE 5

Effect of Free Radical Polymerization initiators on aMVL.

| Monomer | Initiator System | Solvent | Results | Polymer |
|---|---|---|---|---|
| aMVL | AIBN | none | unreacted, darkening | none |
| aMVL | BPO, TMA | C₆D₆ | unreacted | none |
| aMVL | AIBN | C₆D₆ | unreacted | none |
| aMVL | BPO | none | unreacted | none |
| aMVL | DTBP | none | unreacted | none |
| aMVL, styrene | AIBN | C₆D₆ | unreacted | polystyrene |
| aMVL, styrene | BPO | C₆D₆ | unreacted | polystyrene |
| aMVL, styrene | AIBN | CDCl₃ | unreacted | polystyrene |
| aMVL, styrene | BPO | none | unreacted | polystyrene |
| aMVL, MMA | AIBN | C₆D₆ | unreacted | PMMA |
| aMVL, MMA | BPO | C₆D₆ | unreacted | PMMA |
| aMVL, MMA | BPO | none | unreacted | PMMA |

Example 9

Measurement of Dielectric Constant of aMVL

Using 4284A PRECISION LCR METER by Agilent, the impedance of pure aMVL was measured. All electrodes of the LCR meter are immersed in 120 ml of pure anhydrous aMVL solution. The LCR meter was set to series circuit mode to calculate the capacitance of the solution. The capacitance was then converted to the dielectric constant by the following formula:

$$k = C \times \frac{d}{A \times \varepsilon_a}$$

Where k is the dielectric constant, C is the measured capacitance (F), A is the area of the electrodes and εo is the dielectric constant of vacuum. Comparison of the dielectric constant vs other solvents is given in Table 6.

TABLE 6

| Comparison of dielectric constant of aMVL vs other commonly used capacitor electrolytes. | |
| --- | --- |
| Compound | Dielectric constant |
| aMVL | 48.3 |
| Gamma butyrolactone (GBL) | 40.2 |
| N-methyl-2-pyrrolidone (NMP) | 31.1 |
| Methanol | 30 |
| Ethylene Glycol | 37 |
| $H_2O$ | 80.2 |

Example 10

Use of aMVL in Aluminum Electrolytic Capacitors (Prophetic)

The capacitor element is formed by rolling up an anodic foil and a cathodic foil with a separator intervening in between. The anodic foil used is one obtained in such a manner that an aluminum foil of a purity of 99.9% is subjected to chemical or electrochemical etching in an acidic solution to enhance the surface area thereof and then subjected to a chemical treatment in an ammonium adipate aqueous solution, so as to form an anodic oxide film layer on the surface thereof. The cathodic foil used is an aluminum foil of a purity of 99.9% having been subjected to etching to enhance the surface area thereof.

The capacitor element thus constituted in the foregoing manner is impregnated with pure anhydrous aMVL solution for driving an electrolytic capacitor. The capacitor element impregnated with the electrolytic solution is housed in an aluminum cylindrical outer package with a bottom, a sealing member formed with butyl rubber is inserted into an open end of the outer package, and further, the open end of the outer package is sealed by drawing to seal the aluminum electrolytic capacitor. The assembly is shown in FIGS. 5A, 5B, and 5C.

The aluminum electrolytic capacitors thus constituted can be subjected to a high-temperature service life test. The rating of the aluminum electrolytic capacitors is 50 WV-100 mF. The test conditions are at 125° C. with load of the rated voltage for 1,000 hours, and at 125° C. with no load for 1,000 hours.

Example 11

Paint Removal

Figure 4:
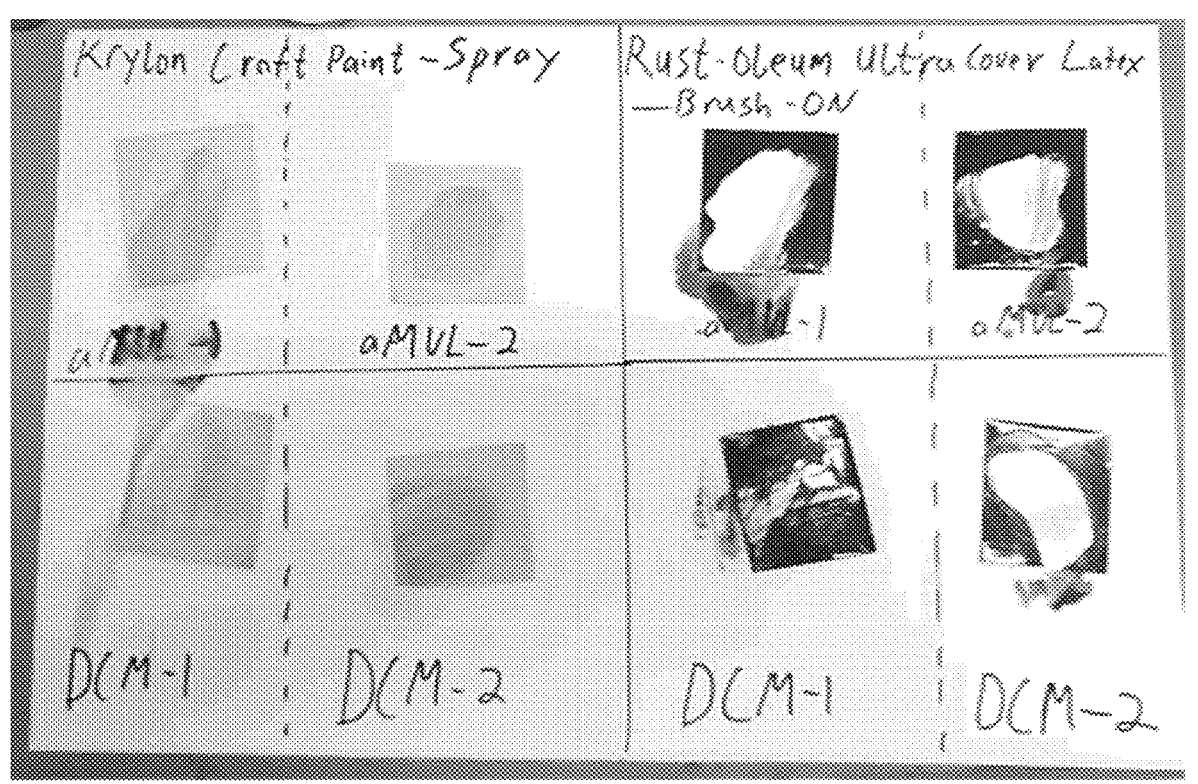
FIG. 4 is a series of photographs showing paint removal by aMVL solvent compared to DCM solvent.

Consumer paint such as Krayton spray paint and Rust-Oleum latex paint was spot painted on a metal surface and allowed to dry over the course of 12 h. Paint removal using aMVL and dichloromethane (DCM) were compared by adding 100 uL of each solution to painted surface and the metal surfaces were gently wiped with a paper towel. FIG. 4 shows visual paint removal by aMVL compared to DCM.

Example 12

Volatility of aMVL for Paint Remover Recycling

Figure 3:
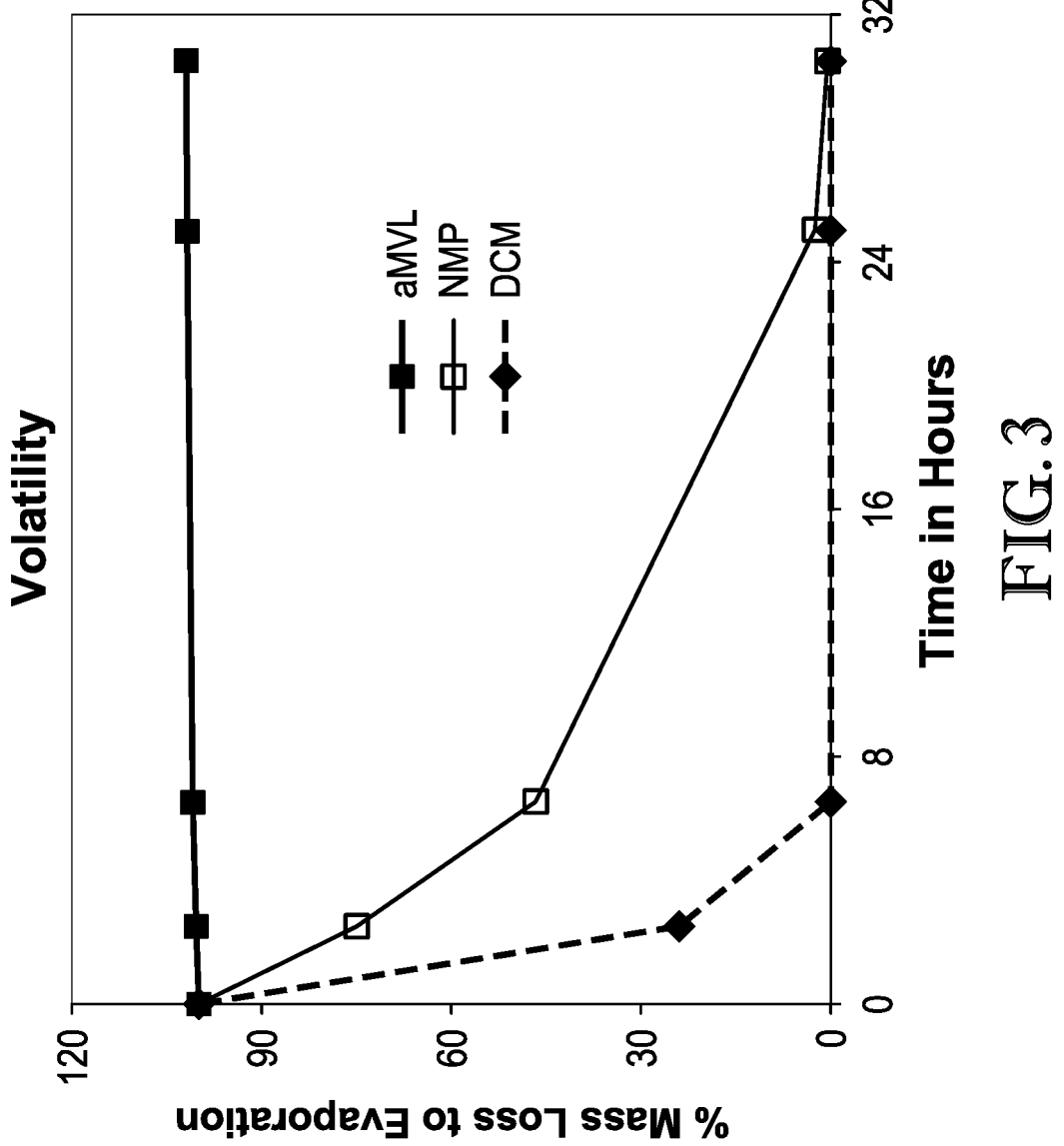
FIG. 3 is a graph showing comparative results of volatility testing of aMVL, DCM, and NMP.

Experiments to compare the volatility of aMVL with that of NMP (N-methyl-2-pyrrolidone) and DCM (dicholoromethane) were performed by preparing samples of each solvent in 20 mL scintillation vials. The samples were left un-capped in a fume hood and weighed at intervals to determine the rate of mass loss. As shown in FIG. 3, aMVL is non-volatile compared to DCM and NMP. This will lead to higher recovery and lower losses when recycled for paint removing applications.

Example 13

Effect of Additives on Paint Removal (Prophetic)

Coating remover compositions can be prepared by combining aMVL and a plant, animal or petrochemical derived oil with optional solvent or thickener components, and mixing until a homogeneous blend was obtained. The additives to test are listed below. Aluminum panels (3"×6") can be painted either with Krayton craft paint or Rust-Oleum latex paint. One coat of approximately 1.5 mm thickness can be applied. Each panel can then be treated with the aforementioned blends in three different spots. Each spot can be ~0.5 to 1.0 inch in diameter. The time necessary to obtain complete bubbling of the coating from the substrate for each spot can then be measured.

The compositions can also be tested for their ability to remove multiple coats of commercially available paint from wood. Pressure-treated pine was painted sequentially with: (a) one coat of white shellac (aged 14 hours), (b) two coats of white alkyd semi-gloss (aged 1 week), (c) two coats of red, flat, outdoor acrylic (aged 1 week), (d) one coat of black, outdoor, alkyd semi-gloss (aged 4 days), (e) one coat of white shellac (aged 1 day), and (f) one coat of white, flat vinyl acrylic (aged 1 month).
Additives:
  Soybean oil
  Corn oil
  Peanut oil
  Olive oil
  Inedible tallow
  Turpentine
  Xylene
  Mineral oil
  Dipropylene glycol methyl ether acetate
  Methyl tert-butyl ether

Example 14

Stain Removal and Household Cleaning (Prophetic)

Solutions of varying concentrations of aMVL (0.5-100 wt %) can be prepared in water. Different carbonaceous deposits, fat residues, vegetable oil and wine stains can be created on cotton cloth no more than 2×2 inches. The aMVL solutions can be applied to these stains and left at different temperatures (20° C., 40° C. and 60° C.) for 24 h. After 24 hours, these cloth patches are washed with water and then dried in a vacuum oven at 80° C. for 2-4 hours. Post drying; these cloth samples can be compared to commercial stain removers and control samples for a qualitative measurement of stain removal.

Example 15

Production of Polyimide Coatings (Prophetic)

To 2 g of aMVL containing a minor amount (about 0.05 to 0.1 percent) of water can be added with stirring, 1.6 grams of 2,2-bis(4-(3,4-dicarboxyphenoxy)-) phenylpropane (4,4'-BPATA) and 0.72 g of 4,4'-methylene dianiline (MDA). Stirring is continued for 3-4 hours, during which time the mixture of ingredients is heated to 45° C. and maintained at that temperature, resulting in formation of a clear, homogeneous, moderately viscous solution. A portion of the solution prepared above can be cast on aluminum foil and heated for 5 minutes at 120° C., 5 minutes at 140° C., and 15 minutes at 160° C. A 3-mil cured polymeric film can be created.

Example 16

Preparation of Polyamide-Imide Coatings (Prophetic)

12.5 g of 2,4'-diphenylmethane-diisocyanate (MDI) plus 237.5 g of 4,4'-MDI (as an isocyanate constituent) and 192 g (1.0 mol) of trimellic acid-anhydride (TMA) (as an acid constituent) can be reacted in aMVL (1000 g) for synthesis. Then, the solution is further diluted with 300 g of N,N-dimethylformamide (DMF). Thus, a polyamide-imide resin based insulating varnish having a resin constituent concentration of approximately 25 mass % is prepared. After that, the varnish can be applied around a 0.8 mm diameter copper wire and baked.

Example 17

Production of Microporous Polysulfone Membranes (Prophetic)

A raw solution for forming a membrane can be prepared by homogeneously dissolving 15 parts polysulfone, 69 parts aMVL, 15 parts of polyvinylpyrrolidone and 1 part water. The solution is allowed to spread over a glass plate with a casting coater so as to have a spread solution thickness of 100-200 μm, and warm air at 40° C. is blown on to the surface of the spread solution samples. The samples are immediately immersed in a solidifying bath containing water at 20° C. to obtain micro-porous membranes.

The average pore size of each of the resulting membranes can determined according to ASTM-f-316-03, and the depth of the dense layer form the surface can be measured with an electron microscope.

Example 18

Production of Fine Porous Polysulfone Membranes (Prophetic)

15 parts polysulfone, 66 parts aMVL, 15 parts polyvinylpyrrolidone, 2 parts lithium chloride, and 2 parts water can be uniformly mixed to prepare a film-forming stock solution. The solution is cast on a glass plate by means of a doctored blade to a thickness of ~200 μm on a dry basis, and 25° C. air is blown at a velocity of 1.0 m/sec and directed to the surface of the cast film. Immediately thereafter, the film is dipped in a coagulating bath filled with water at 25° C. to obtain a fine porous membrane.

The average pore size of each of the resulting membranes can be determined according to ASTM-f-316-03, and the depth of the dense layer form the surface can be measured with an electron microscope.

Example 19

Preparation of Polycarbonate Membranes (Prophetic)

A composition of 52 weight percent tetrabromobisphenol A polycarbonate, 32.5 weight percent aMVL (solvent) and 15.5 weight percent triethylene glycol (TEG) (non-solvent), (solvent to non-solvent ratio of ~2:1) can be fed into the melt pot of a melt pot extruder. Dichloromethane (DCM) in an amount equal to 30 weight percent of the total composition is added to the melt pot. The mixture is heated to 95° C. at least until the mixture becomes a homogeneous solution. Most of the DCM will flash off during this heating step. A nitrogen purge is passed into the melt pot at 500 cubic centimeters per minute, and nitrogen containing volatilized DCM is withdrawn from the melt pot. From the melt pot, the mixture is passed to a transfer line and pumped to a hollow fiber spinnerette at a flow rate of around 15 grams per minute.

The transfer line and spinnerette face are held at a temperature of 75° C. The mixture is extruded into a hollow fiber through an annulus of 254 microns with an outside diameter of ~1800 microns with a core gas pin feeding a core gas of nitrogen down the bore at a rate of 8.8 standard cubic centimeters per minute. The line speed is 100 feet per minute. The hollow fiber is extruded into an air quench zone of a length of 1 foot at ambient temperature. The fiber is passed into a quench bath of water at 4° C. with a residence time of 2 seconds. The fiber is taken up and thereafter placed in a bath of water at 90° C. for ten minutes. The fiber is hung vertically and dried by passing air at a flow rate of 100 feet per minute over the fibers for two hours.

The hollow fiber membranes prepared can be examined by scanning electron microscopy (SEM) and the average pore size can be measured according to ASTM f-316-03. Such membranes have a porous outer and inner surface.

Example 20

Preparation of Graphene-PHB Nanocomposites (Prophetic)

The biopolymer polyhydroxybutyrate (PHB) can be dissolved in aMVL at a concentration of 33 mg/ml of solvent with stirring at 120° C. Graphene dispersion is prepared but not centrifuged to maximize the quantity of dispersed graphene/graphite present (5 ml). This is then deposited on a 0.2 μm Fluoropore™ membrane during suction to leave behind a graphene/graphite film on the membrane. Afterwards, the polymer solution is poured on top and left to cool, creating a bilayer film. The sample is first washed thoroughly with water. It is then placed in a vacuum oven at 120° C. for 24 hours to remove any residual water.

Example 21

Preparation of Polylactic Acid Resin Microparticles (Prophetic)

1.5 g of polylactic acid (Molecular weight-160,000), 2.5 g of hydroxypropyl cellulose as polymer different from polylactic acid and 46 g of aMVL can be put in a 100 ml autoclave, heated to 50° C., and stirred until the polymers are completely dissolved. After cooling back to room temperature, 50 g of deionized water as a poor solvent is added by dripping it with a pump at a speed of 0.4 g per minute while stirring at 500 RPM. Stirring is continued for another 30 minutes after the whole amount of water has been added, and the resulting suspension is filtered and washed three times with 50 g of deionized water. The filtered matter is then dried under vacuum at 80° C. for 10 hours to obtain ~0.5 g white solid in powder form. The powder obtained can be analyzed via a Scanning Electron Microscope (SEM) to measure the average particle diameter and particle diameter distribution index.

Example 22

Preparation of PAN Films for Use as a Battery Separator (Prophetic)

A battery separator can be formed by a thermally-induced phase separation method in which polyacrylonitrile (PAN) is dissolved in a miscible mixture of, 95% aMVL and 5% water by wt. at 80° C. to form a single phase solution containing 10% by wt. PAN. Particles of Aerosil R805 (hydrophobic treated fumed silica particles) are then added to the single phase polymer solution. The amount of these particles added is 10 wt. % based on the weight of the PAN. A film of the polymer solution is then cast onto a flat glass plate and allowed to cool. During cooling, the film transforms from clear to opaque as the PAN precipitated. The aMVL is then extracted by washing the solid PAN precipitate with water. Afterwards, the solid PAN precipitate is dried, with heat, to evaporate any residual water to produce the separator.

Example 23

Preparation of Polyethersulfone (Prophetic)

Into a reactor having an internal capacity of 100 ml, 1.141 g of bisphenol A, 0.835 g of an aqueous sodium hydroxide solution (48.40% by weight) and 5 ml of aMVL can be charged. After flushing the air in the reaction system with nitrogen, the mixture is heated to 150° C. under stirring at 300 RPM and maintained at that temperature for 10 minutes. Then, the reaction mixture is cooled to a temperature below 100° C. and 0.647 g of sodium sulfide (purity: 60%) and 20 ml of chlorobenzene is added. The mixture is heated again, and water present in the reaction mixture is continuously removed as an azeotrope with chlorobenzene. After the chlorobenzene is thoroughly distilled off, the reaction mixture is heated to 150° C. for 10 minutes. Then, the reaction mixture is cooled to 40° C., and 2.872 g of 4,4'-dichlorodiphenyl sulfone and 5 ml of aMVL are added. After thoroughly flushing the inside of the reaction system with nitrogen, the mixture is heated to 150° C. and reacted for 14 hours. The reaction product thus obtained is poured into a large amount of methanol, whereby a white polymer precipitated. The polymer is collected by filtration, washed twice with methanol and twice with hot water and dried under reduced pressure at 100° C. for 5 hours. ~3 g of solid white polymer powder is obtained.

Example 24

Preparation of Poly(Vinyl Cinnamate) (Prophetic)

11 g of medium molecular weight, highly hydrolyzed polyvinyl alcohol can be gradually added with stirring to 100 ml aMVL at room temperature in a 500 ml, 3-necked flask with a stirrer, thermometer, condenser, with drying tube attached. The mixture is heated and stirred on a steam bath at 90° C. overnight. An additional 100 ml of aMVL is added the next morning at 90° C. and the solution of polyvinyl alcohol is cooled to 50° C. 50 g of molten cinnamoyl chloride is added by means of a heated dropping funnel to the reaction mixture at around 50° C. for 20 minutes. The temperature is held at 50° C. for 4 hours. The reaction mixture is poured slowly with rapid stirring into a solution of 64 g of sodium carbonate and 2 liters of water. The precipitated polymer is shredded several times with water in a Waring Blender, the product filtered on a Buchner funnel after each treatment. After drying in a vacuum oven at 60° C., roughly 40 g of the cinnamate ester of polyvinyl alcohol is obtained.

The invention claimed is:

1. A composition comprising:
   (a) from about 75 to about 95 weight percent of anhydromevalonolactone; and
   (b) from about 5 to about 25 weight percent of a polymer selected from the group consisting of a polyacrylonitrile, a polycarbonate, a polylactic acid, a polyetherimide, a polystyrene, a polymethyl methacrylate (PMMA), a polyvinyl chloride, and a nylon, wherein said polymer is dissolved in the anhydromevalonolactone at 80° C. and/or 150° C.

2. The composition of claim 1, wherein said composition exhibits one or more of the following characteristics:
   (a) wherein said composition has a boiling point of about 200 to about 250° C.,
   (b) wherein said composition has a melting point of about −40 to about 20° C.,
   (c) wherein said composition has a viscosity of about 3 to about 5 mPa at standard ambient temperature and pressure,
   (d) wherein said composition has a water solubility of about 600 to about 900 g/L at standard ambient temperature and pressure, or
   (e) wherein said composition has a vapor pressure of about 30 to about 40 Pa at 67° C.

3. The composition of claim 1, further comprising a co-solvent selected from the group consisting of methyl ethyl ketone, benzyl acetate, ethyl benzoate, cyclohexanone, cyclopentyl methyl ether, and dichloromethane.

4. The composition of claim 1, wherein said composition exhibits a boiling point of about 200 to about 250° C.

5. The composition of claim 1, wherein said composition exhibits:
   (a) a boiling point of about 200 to about 250° C.,
   (b) a melting point of about −40 to about 20° C.,
   (c) a viscosity of about 3 to about 5 mPa at standard ambient temperature and pressure,
   (d) a water solubility of about 600 to about 900 g/L at standard ambient temperature and pressure, and
   (e) a vapor pressure of about 30 to about 40 Pa at 67° C.

6. The composition of claim 1, wherein said composition further comprises water.

7. The composition of claim 1, wherein said polymer is the polyacrylonitrile.

8. The composition of claim 1, wherein said polymer is the polylactic acid.

9. The composition of claim 1, wherein said polymer is the PMMA.

* * * * *